US008628513B2

(12) United States Patent
Duffy et al.

(10) Patent No.: US 8,628,513 B2
(45) Date of Patent: Jan. 14, 2014

(54) CELL RESERVOIRS CREATED BY POLYMER PLUGS

(75) Inventors: Angela Duffy, Galway (IE); Brendan Hanley, Galway (IE); Padraic Curran, Windsor, CA (US); Michael Benz, Ramsey, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 452 days.

(21) Appl. No.: 12/755,470

(22) Filed: Apr. 7, 2010

(65) Prior Publication Data

US 2011/0251545 A1 Oct. 13, 2011

(51) Int. Cl.
*A61M 31/00* (2006.01)
(52) U.S. Cl.
USPC .............................. 604/522; 604/523; 604/21
(58) Field of Classification Search
USPC ............ 604/508, 96.01, 164.01, 523, 522, 21
See application file for complete search history.

(56) References Cited

U.S. PATENT DOCUMENTS

| 2004/0186422 | A1  | 9/2004  | Rioux et al. |
| 2006/0004325 | A1  | 1/2006  | Hamatake et al. |
| 2006/0009740 | A1  | 1/2006  | Higgins et al. |
| 2007/0106259 | A1* | 5/2007  | Epstein et al. ................ 604/509 |
| 2008/0065048 | A1* | 3/2008  | Sabbah et al. ................ 604/511 |
| 2008/0086081 | A1* | 4/2008  | Eidenschink et al. ..... 604/96.01 |
| 2008/0255447 | A1  | 10/2008 | Bourang et al. |

FOREIGN PATENT DOCUMENTS

| WO | WO2004/000692 | 12/2003 |
| WO | WO2009/049823 | 4/2009 |

* cited by examiner

*Primary Examiner* — Kevin C Sirmons
*Assistant Examiner* — Brandy S Lee

(57) ABSTRACT

Described herein generally are catheter systems used to deliver cells and other bioactive materials to a target location within the vascular system of the human body, and methods of delivering cells and other bioactive materials to such target locations.

19 Claims, 3 Drawing Sheets

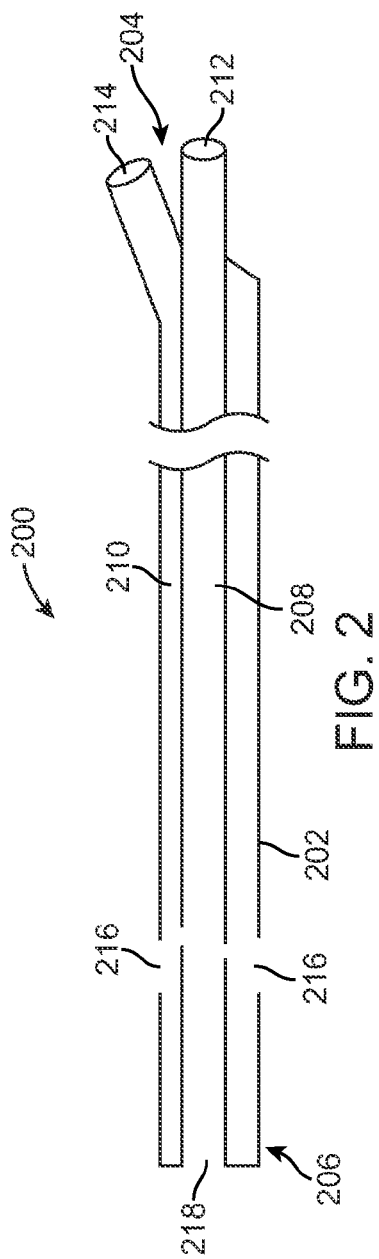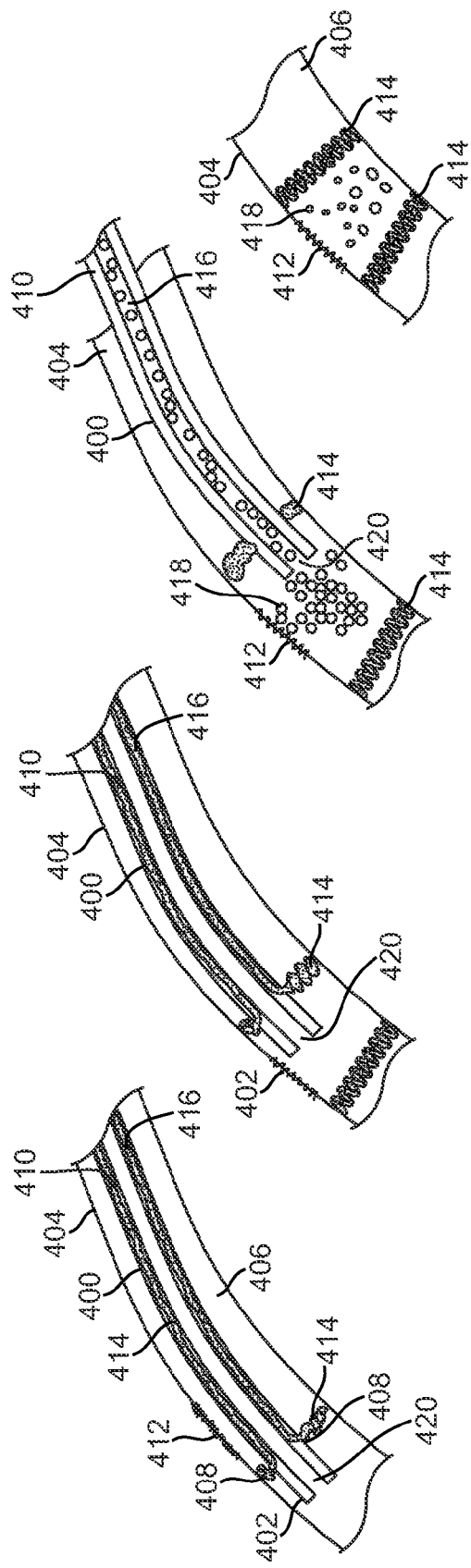

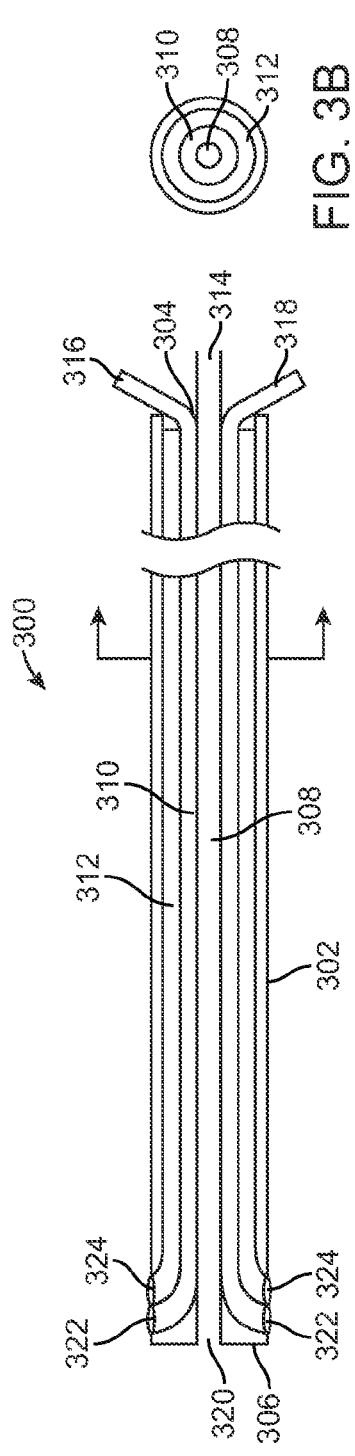
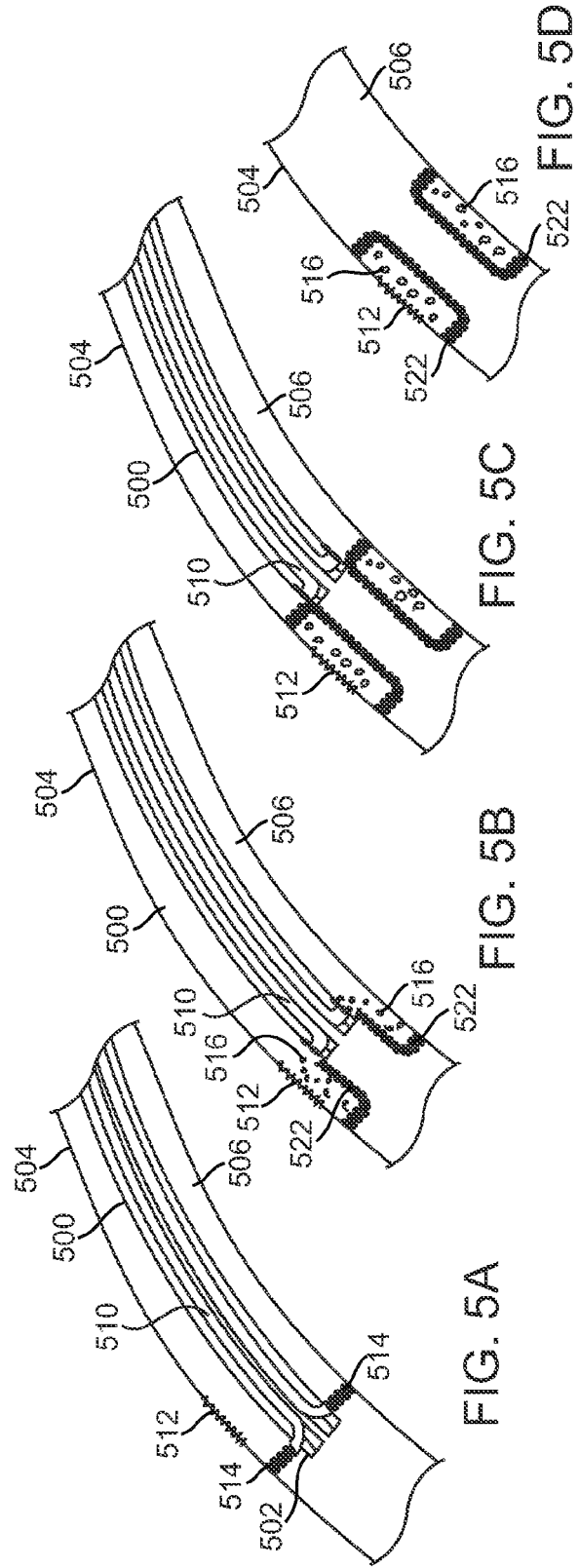

CELL RESERVOIRS CREATED BY POLYMER PLUGS

FIELD OF THE INVENTION

Cell delivery systems, associated apparatus and methods of using the same.

BACKGROUND

Cardiovascular disease is a leading cause of death in the United States. During the last few decades, a number of treatment methods and devices have been developed to combat the disease and treat the resulting complications.

One method developed to treat cardiovascular disease is local therapy at the site in question. Delivery catheters have been used extensively in delivering local therapy. For example, they can be used to deliver stents, grafts, therapeutic substances and radiopaque agents to a desired location within the patient's vasculature.

Therapeutic substances such as cells and other bioactive materials are often introduced into the tissue in question in order to treat a disease or condition. Various methods of cell delivery have been employed with varying degrees of success. Direct cell delivery has been used when an increased cell density is desired at the target site. Although direct cell delivery has been shown to increase the number of viable cells in some target locations, a significant problem still exists when the cells are delivered to localized vasculature. When cells and/or bioactive materials are delivered to blood vessels, a majority of the delivered materials dissipate or redistribute from the target site due to the natural flow of blood through the vessel. Specific targeted delivery of cells such as stem cells to the treatment area can also be a challenge. Circulating blood can wash out the stem cells that are injected to a target site such as a heart muscle wall.

Therefore, a need exists for improved cell delivery to blood vessels in the human body that overcomes these and other disadvantages.

SUMMARY

Accordingly, described herein are catheter systems including a catheter with an elongated tubular member having a distal end and a proximal end, with multiple entry and exit ports. Multiple lumens are provided within the catheters described. A lumen, for example, can be sized and shaped to receive a movable guidewire and one or more bioactive materials. The catheter system can further comprise a lumen traversing through the elongated tubular member sized and shaped to receive one or more polymers.

Methods of using the catheter systems are also described. In one embodiment, methods of delivering at least one bioactive material to a vessel in need thereof are described comprising the steps of first selecting a target site within the vessel in need of the at least one bioactive material. Then, providing a catheter comprising an elongated tubular member having a distal end and a proximal end is provided, wherein the proximal end is attached to at least one delivery means, a first lumen longitudinally traversing through the elongated tubular member having the ability to receive at least one bioactive material, wherein the first lumen includes an exit port at the distal end, and a second lumen longitudinally traversing through the elongated tubular member having the ability to receive at least one polymer, wherein the second lumen includes at least one exit port proximal to the distal end. The distal end of the catheter is then positioned so that it is distal to the target site, after which the at least one polymer is delivered through the at least one exit port in the second lumen creating a first plug member. The catheter is next repositioned so that the distal end is proximal to the first plug member and the at least one bioactive material is delivered through the exit port in the first lumen between the first plug member and the second plug member. To finish, the catheter is removed from the vessel thereby delivering the at least one bioactive material.

BRIEF DESCRIPTION OF THE DRAWINGS

The figures included herein show by way of illustration specific embodiments in which the present inventions may be practiced. It is to be understood that other embodiments may be utilized and structural changes may be made without departing from the scope of the present invention.

FIG. 2 illustrates a plan view of a generalized multilumen catheter according to an example embodiment.

FIGS. 3 A-B illustrate a plan view of a generalized multilumen catheter according to an example embodiment.

FIGS. 4A-D illustrate section views of the distal end of a coaxial multilumen catheter in a blood vessel according to a present embodiment. FIG. 4A illustrates the first delivery of a polymer to a location distal to the target site through at least one exit port of the second or outer lumen. FIG. 4B illustrates the second delivery of the polymer to a location proximal to the location at which the first polymer was delivered. FIG. 4C illustrates the delivery of a bioactive material to a location between the first and second location at which polymers were delivered. FIG. 4D illustrates the target site after the catheter is removed.

FIGS. 5A-D illustrate section views of the distal end of a coaxial multilumen catheter in a blood vessel according to a present embodiment. FIG. 5A illustrates the first delivery of a polymer to a location distal to the target site through at least one exit port of the second or outer lumen. FIG. 5B illustrates the delivery of the polymer as the catheter is advanced past the target site concurrently the bioactive material is delivered. FIG. 5C illustrates the second delivery of the polymer to a location proximal to the location at which the first polymer was delivered. FIG. 5D illustrates the target site after the catheter is removed.

DEFINITION OF TERMS

Figure 1:
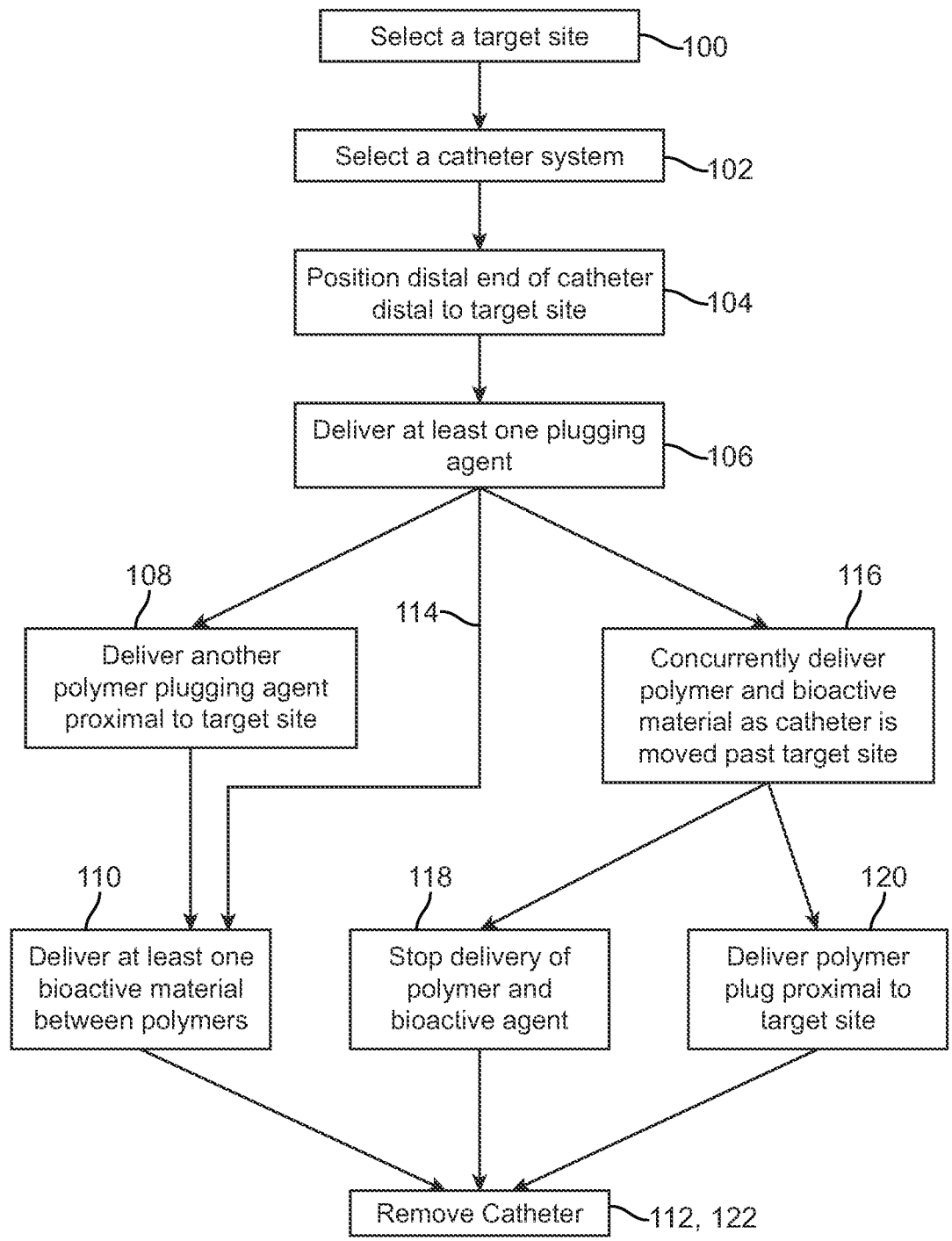
FIG. 1 illustrates a flow chart of steps used to practice the methods described herein.

Certain terms as used in the present specification are intended to refer to the following definitions, as detailed below. Where the definition of terms departs from the commonly used meaning of the term, the definitions provided below can be utilized, unless specifically indicated.

As used herein, "bioabsorbable" materials are materials that through naturally occurring mechanisms can be broken down and absorbed or simply absorbed within the human body and/or excreted from the body. All bioabsorbable materials are considered biodegradable.

The term "biocompatible", as used herein, refers to having the property of being biologically compatible by not producing a toxic, injurious, or immunological response in living tissue.

"Biodegradable" materials are materials that can degrade over time by naturally occurring mechanisms in the human body.

The terms "reversibly gelling" and "reverse thermosensitive" refer to the property of a polymer wherein gelation takes place upon an increase in temperature, rather than a decrease in temperature. The term "reverse thermosensitive polymer" as used herein refers to a polymer that is soluble in water at ambient temperature, but at least partially undergoes a phase transition to form a gel or solid at physiological temperature.

DETAILED DESCRIPTION

Described herein generally are methods and systems for delivering at least one bioactive material to a vessel in need thereof. The devices themselves overcome the long felt need to deliver bioactive materials such as cells to a hemodynamic environment such as an injured or diseased vessel, where in the past, therapy at a specific location has not been possible for any appreciable amount of time. The methods and systems described allow accurate delivery of bioactive/therapeutic materials to a target site and significantly decrease the dissipation or washing out of delivered bioactive material. Overall, this will increase the efficacy and duration of treatment at the target site.

FIG. 1 illustrates a flow chart of steps generally taken according to the methods described herein. The first step 100 is to select a target site. A target site is within a vessel of a mammal, preferably a human. The target site can be injured (e.g. punctured, torn, or swollen) and/or diseased (e.g. atherosclerosis or aneurysm) and in need of treatment. In one embodiment, the system impedes blood flow through the vessel to be treated, and therefore, the methods and systems described herein can be used in coronary vessels whose blockage would not affect heart function (e.g. venous vessels or distal arteries). In another embodiment, the methods and systems do not entirely impede blood flow through the vessel for an appreciable amount of time, so vessels affecting heart function can be treated.

If blood flow is substantially impeded, the vessel is preferably a non-vital vessel which can be without blood flow for a given amount of time. An exemplary vessel might be a vein wherein redundancy is not as critical as the arterial network. If blood flow is not to be substantially impeded or not substantially impeded for a long period of time, the systems and methods described herein can be used in the arterial system, preferably, distal vessels would be targeted.

The next step 102 is to select an appropriate catheter system by which at least one bioactive material will be delivered to the selected target site. FIG. 2 illustrates an exemplary multilumen catheter 200. Catheter 200 includes, without limitation, an elongated tubular member or shaft 202 having a proximal end 204, a distal end 206 and at least two parallel lumens extending longitudinally therebetween within elongated shaft 202. The parallel lumens may be coaxially mounted tubes with first lumen 208 inside second lumen 210, and each with at least one separate and distinct entry port 212, 214 and exit port 216, 218. Alternatively, the parallel lumens may extend longitudinally adjacent to one another within the shaft, having complementary contours, each with at least one separate and distinct entry port and exit port.

First lumen 208 may have at least one entry port 212 at proximal end 204 of catheter 200, at least one exit port 218 at distal end 206, and a luminal body traversing longitudinally through elongated tubular member 202. First lumen 208 is sized and shaped to receive at least one bioactive material and may also be sized and shaped to receive a movable guidewire (not illustrated) through at least a portion of the catheter.

Second lumen 210 may have at least one entry port 214 at proximal end 204 of catheter 200, at least one exit port 216 proximal to distal end 206, and a luminal body traversing longitudinally through elongated tubular member 202. Second lumen 210 is sized and shaped to receive at least one polymer.

The catheters described herein may be formed such that the first lumen may be the inner lumen of a multilumen coaxial catheter system. The first lumen may have one exit port at the distal end of the catheter. The first lumen may have at least one exit port distal to the exit port(s) of the second or outer lumen. The first lumen may extend further distally than the second or outer lumen and each lumen may have at least one exit port at its distal end. Alternatively, both lumens may end at the distal end of the catheter but the exit port(s) of the second lumen may be proximal to the exit port(s) of the first lumen.

An alternate embodiment of a catheter is illustrated in FIGS. 3A and 3B. Trilumen catheter 300 includes, without limitation, an elongated tubular member or shaft 302 having a proximal end 304, a distal end 306 and at least three parallel lumens extending longitudinally therebetween within elongated shaft 302. The parallel lumens may be coaxially mounted tubes with first lumen 308 inside second lumen 310 which is inside third lumen 312, and each with at least one separate and distinct entry port 314, 316, 318 and exit port 320, 322, 324. The exit ports make at least a partial circumferential exit from the catheter. In a preferred embodiment, the exit ports span the entire circumferential area of the catheter.

First lumen 308 may have at least one entry port 314 at proximal end 304 of catheter 300, at least one exit port 320 at distal end 306, and a luminal body traversing longitudinally through elongated tubular member 302. First lumen 308 is sized and shaped to receive a movable guidewire (not illustrated) through at least a portion of the catheter.

Second lumen 310 may have at least one entry port 316 at proximal end 304 of catheter 300, at least one exit port 322 proximal to distal end 306, and a luminal body traversing longitudinally through elongated tubular member 302. Second lumen 310 is sized and shaped to receive at least one polymer.

Third lumen 312 may have at least one entry port 318 at proximal end 304 of catheter 300, at least one exit port 324 proximal to distal end 306, and a luminal body traversing longitudinally through elongated tubular member 302. Second lumen 312 is sized and shaped to receive at least one bioactive material.

The next step 104 is to position the distal end of the catheter so that it is distal to the target treatment site. A guidewire fed through one of the lumens within the catheter, preferably one that is most centered, can be used to navigate the distal end of the catheter to the appropriate position within the vessel. Other methods of catheter navigation are well known in the art and are within the scope of the present description.

FIGS. 4A-D illustrate how at least one bioactive material is delivered using the catheter system illustrated in FIG. 2. After inserting distal end 402 of multilumen catheter 400 into vessel 404 through vessel lumen 406 so that exit port(s) 408 of second lumen 410 are distal to target site 412, the actual delivery of the at least one bioactive material can commence. The external, proximal end of the multilumen catheter may be affixed to the patient, and a delivery device may be affixed to the external, proximal end of each lumen of the multilumen catheter (not illustrated).

As a next step 106, a delivery device affixed to the proximal end of the second lumen may deliver a first dose of at least one polymer plugging agent 414. Plugging agent 414 will traverse the body of second lumen 410 and may be deposited into vessel 404 at a point distal to target site 412, through exit port(s) 408 of second lumen 410.

The at least one polymer or polymer plugging agent may include any material capable of creating a seal and preventing the dispersion of bioactive materials once delivered. Typically, the at least one polymer may comprise biocompatible polymers. Such polymers may be biodegradable, bioabsorbable and/or biostable. Alternatively, the at least one polymer may include non-biodegradable materials such as silicones, aluminates, and elastomers.

The at least one polymer may be delivered to the target location in a non-fluent state or in a fluent state, where conditions in situ cause the at least one polymer to solidify to a less-fluent or non-fluent state. "Fluent" as used herein is meant to describe a polymers ability to flow. The decreased fluency can be a passive change occurring when the at least one polymer is delivered to the target site, or alternatively, may be caused by the addition or removal of certain chemicals or an induced change in the surrounding environment. More specifically, the altered in vivo conditions may be the result of changes in temperature or pH, or the application of light, ultrasound, radiation, chelation, or chemical catalysts. The transition may be the result of a phase change, viscosity change or polymerization of the at least one polymer when delivered to the target site.

In general, the polymers of the present invention can be administered in a liquid form or a solid or gel form. In certain embodiments, the polymer composition may be a flexible or flowable material. "Flowable" includes the ability to assume, over time, the shape of the space containing it at body temperature. This characteristic includes, for example, liquid compositions that are suitable for injection through a delivery catheter. Also encompassed by the term "flowable" are highly viscous, gel-like materials at room temperature that may be delivered to the desired site by being injected into the second lumen with any one of the commercially available power injection devices that provide injection pressures greater than would be exerted by manual means alone. In some instances, the polymer may be flowable only when combined with a biocompatible solvent. In other instances, the polymer itself may be flowable and therefore, will not need to include a biocompatible solvent, although trace or residual amounts of biocompatible solvents may be present.

The polymer solution may be a solution of one or more reverse thermosensitive or "smart" polymers. These polymer solutions are liquids below body temperature and gel at or about body temperature. In certain embodiments, the polymer solution is prepared at a temperature below body temperature. The polymer solution may be further chilled to prolong the time the gel stays in the liquid form upon introduction into the body. A preferred temperature is about 10° C. below the gelation temperature of the polymer solution.

In certain embodiments, the polymer may comprise thermosensitive natural polysaccharides. Examples of natural polysaccharides include, but are not limited to, methylcellulose solutions with sodium chloride to lower their transitional temperatures to 37° C., ethyl(hydroxyethyl) cellulose solutions (EHEC) with surfactants to increase their transitional temperature to 37° C., and chitosan with or without polyol salts (e.g. β-blycerophosphate).

Other thermosensitive polymers include poly(N,N-diethylacrylamide) (PDEAAm); poly(N-iso-propylacrylamide) (PNIPAM) co-polymers, for example poly(NIPAM-co-acrylamide), PNIPAM/polyethylene oxide; poloxamer systems, for example block co-polymers of polyethylene oxide (PEO), block co-polymers of polypropylene oxide (PPO), co-polymers of PEO-PPO-PEO, co-polymers of poloxamer/poly (acrylic acid) (PAA) such as PAA-g-poloxamer and poloxamer-g-PAA; PEO/D,L-lactic acid-co-glycolic acid (PLGA) hydrogels, for example PEO-b-PLGA-b-PEO, PLGA-g-PEO, PEO-g-PLGA; Calcium loaded liposomes (CLL) which form gels when combined, for example CLL with fibrinogen and hrFXIII at 37° C., CLL with thrombin and hrFXIII at 37° C., CLL with FEK16 at 37° C.; poly(organophosphazene) derivatives; and poly(1,2-propylene) phosphate.

Alternatively, the block copolymers may be poloxamers and poloxamines. Poloxamers such as PLURONIC® polymer or poly(acrylic acid)-g-poloxamer and poloxamer-g-poly(acrylic acid) have unique surfactant abilities as well as extremely low toxicity and immunogenic responses. These products have low acute oral and dermal toxicity and low potential for causing irritation or sensitization, and the general chronic and sub-chronic toxicity is low.

Importantly, several reverse sensitive polymers including, poloxamer 188, poloxamer 407, poloxamer 338, poloxamine 1107 and poloxamine 1307 show inverse thermosensitivity within the physiological temperature range. In other words, these polymers are members of a class that are soluble in aqueous solutions at low temperature, but gel at higher temperatures. Poloxamer 407 is a biocompatible polyoxypropylene-polyoxyethylene block copolymer having an average molecular weight of about 12,500 and a polyoxypropylene fraction of about 30%; poloxamer 188 has an average molecular weight of about 8400 and a polyoxypropylene fraction of about 20%; poloxamer 338 has an average molecular weight of about 14,600 and a polyoxypropylene fraction of about 20%; poloxamine 1107 has an average molecular weight of about 14,000, poloxamine 1307 has an average molecular weight of about 18,000. Polymers of this type are also referred to as reversibly gelling because their viscosity increases and decreases with corresponding changes in temperature.

Such thermosensitive polymers can be modified to achieve sol-gel conversion at body temperature. The polymers can be further modified to degrade at a particular temperature and/or rate. For example, the biodegradable capacity of PEO-PPO-PEO block co-polymers can be augmented by replacing the PPO segment with poly(L-lactic acid).

Other smart polymers include polymers sensitive to pH such as, but not limited to, natural polysaccharides, for example chitosan; block co-polymers, for example poly-2-hydroxyethyl methacrylate (HEMA) and poly(methyl methacrylate) PMAA-polyethylene glycol (PEG) block copolymers; hydrogels, for example those made of PAA or poly 9-N,N'-diethylaminoethyl methacrylate); and poly(vinylacetaldiethylaminoacetate) (PVD).

Further still, terpolymer hydrogels responsive to both temperature and pH are contemplated such as, but not limited to, hydrogels made of NIPAAm, vinyl terminated poly-dimethylsiloxane macromer and acrylic acid, and hydrogels made of NIPAAm, acrylic acid and 2-hydroxyethyl methacrylate.

Additionally, certain peptides can be used to make hydrogels more biodegradable. These peptides can be synthetic and include, but are not limited to poly(hydroxyl-L-glutamate), poly(L-or-nithine), poly(aspartic acid), poly(L-lysine) and poly-(L-glutamic acid).

After at least one polymer has been delivered proximal to the target site, the next step 108 involves providing an additional polymer distal to the target site. Catheter 400 may then be pulled proximally so that exit port(s) 408 of second lumen 410 are proximal to target site 412 and a second dose of plugging agent 414 may then be delivered.

Then, at step 110, as the first and second doses of plugging agent 414 gel or solidify, a delivery device affixed to the proximal end of first lumen 416 may deliver a first dose of bioactive material 418, through the body of first lumen 416 to second exit port 420 of first lumen 416 situated at target site 412. This process can be repeated several times, using the same or different bioactive material each time, until the desired amount of bioactive material has been delivered to or near target site 412.

The at least one bioactive material may include a cell or cells. The types of cells included will vary depending on the target site or the surrounding area. Sources of cells suitable for use as a treatment agent can include, but are not limited to, embryonic, fetal, post-natal, adult stem or progenitor cells. More specifically, a treatment agent can include, for example, cardiomyocytes, skeletal myocytes, skeletal myoblasts, mesenchymal stem cells, endothelial progenitor cells, hematological cells, immune cells, and combinations thereof. These cells can be natural or genetically engineered cells that secrete specific hormones or proteins, or that provide certain metabolic functions. Sources of stem cells include, but are not limited to, bone marrow, blood, adipose tissue, gonads, skeletal or cardiac muscle, or any tissue containing stem cells. Such cells can be autologous, homologous or heterologous and can be obtained and prepared for delivery by any suitable method as would be known to persons of ordinary skill in the art.

The at least one bioactive material may include therapeutic agents such as, for example, transforming growth factor beta (TGFβ) and TGF-β-related proteins, angiogenesis-related cytokines, such as vascular endothelial growth factor (VEGF) and hepatocyte growth factor (HGF), anti-thrombogenic agents or other agents for suppressing stenosis or late restenosis such as heparin, streptokinase, urokinase, tissue plasminogen activator, anti-thromboxane $B_2$ agents, anti-B-thromboglobulin, prostaglandin E, aspirin, dipyridimol, anti-thromboxane $A_2$ agents, murine monoclonal antibody 7E3, triazolopyrimidine, ciprostene, hirudin, ticlopidine, nicorandil, and anti-platelet derived growth factor. These and other bioactive materials may be used in combination, and may be used in conjunction with cell delivery.

The at least one bioactive material can be delivered with a pharmaceutically acceptable carrier. Examples of pharmaceutically acceptable carriers include excipients, lubricants, binders, disintegrants, disintegration inhibitors, absorption promoters, adsorbers, moisturizing agents, solvents, solubilizing agents, suspending agents, isotonic agents, buffers, soothing agents and the like.

Acceptable carriers, excipients or stabilizers used herein may be nontoxic to recipients and inert at the dosages and concentrations employed, and may include buffers such as phosphate, citrate, or other organic acids; ascorbic acid, α-tocophenol; low molecular weight polypeptides; proteins (e.g., serum albumin, gelatin, or immunoglobulins); hydrophilic polymers (e.g., polyvinylpyrrolidone); amino acids (e.g., glycine, glutamine, asparagine, arginine or lysine); monosaccharides, disaccharides, and other carbohydrates (including glucose, mannose, or dextrins); chelating agents (e.g., EDTA); sugar alcohols (e.g., mannitol or sorbitol); salt-forming counterions (e.g., sodium); and/or nonionic surfactants (e.g., tween, pluronics or polyethylene glycol (PEG)). One exemplary carrier includes alginate, a biocompatible polymer that is soluble in water, but gels in the presence of divalent metal ions such as calcium.

Then, at step 112, catheter 400 is removed and at least one bioactive material remains between subsequent polymer plug material. Bioactive material is allowed to interact with the tissue at treatment site 412 without being disrupted by blood flow through the region.

In an alternate embodiment, the steps of delivering at least one bioactive agent and then plugging the vessel with at least one polymer are repeated to create additional polymer plug members proximal to the second polymer plug member and wherein the one or more bioactive materials are delivered between the additional polymer plug members.

In an alternate embodiment, simplified process 114, step 108 can be skipped and at least one bioactive material can be delivered following step 106. In such a procedure, the at least one bioactive agent is trapped by the polymer delivered during step 106 and blood flow sequesters the at least one bioactive material at the target site.

FIGS. 5A-D illustrate how at least one bioactive material is delivered using the catheter system illustrated in FIG. 3. After inserting distal end 502 of trilumen catheter 500 into vessel 504 through vessel lumen 506 so that the exit port(s) 508 of second lumen 510 are distal to target site 512. The external, proximal end of the multilumen catheter may be affixed to the patient, and a delivery device may be affixed to the external, proximal end of each lumen of the multilumen catheter (not illustrated).

As a next step 116, a delivery device affixed to the proximal end of the second lumen may deliver at least one polymer or plugging agent 514. Plugging agent 514 will traverse the body of second lumen 510 and may be deposited into vessel 504 at a point distal to target site 512, through exit port(s) 508 of second lumen 510. The polymer seals the area between the vessel wall and the catheter itself as illustrated in FIG. 5A.

Then, the catheter is moved through the vessel past the target site 512. Concurrently, the at least one polymer is delivered through second lumen 510 and out exit port 508 and at least one bioactive material 516 is delivered through second lumen 518 and out exit port 520 thereby trapping the bioactive material within a created polymeric structure 522.

At this point, once the bioactive material is trapped, the next step 118 can commence. Delivery of both the bioactive material and the at least one polymer is stopped and the catheter is removed and the at least one bioactive material is allowed to interact with the tissue at treatment site 512 without being substantially disrupted by blood flow through the region. After catheter 500 is removed, blood flow through the region is restored.

In another embodiment, step 120, after delivery of both the bioactive material and the at least one polymer is stopped, an additional polymer plug distal to the target site is distributed. Catheter 500 is pulled proximally to the target site 512 so that exit port(s) 508 of second lumen 510 are proximal to target site 512 and a second dose of polymer 514 may then be delivered. The delivery of polymer seals the bioactive material within a polymer structure 522.

Then, at step 122, catheter is removed and at least one bioactive material remains within polymer structure 522. Bioactive material is allowed to interact with the tissue at treatment site 512 without being disrupted by blood flow through the region. After catheter 500 is removed, blood flow through the region is restored.

The polymers utilized herein to form plugs or encasements for bioactive materials can impede or partially impede blood flow through a treated vessel. Depending on the location of treatment and the polymer itself, the plug or encasement can last for an hour, several hours, a day, a week, a month or even indefinitely.

For example, in one example embodiment, if the polymer used to form a plug or encasement is made of a biostable polymer (e.g., silicones or some polyurethanes), it could potentially last the lifetime of the patient.

In contrast, in the case of biodegradable polymers, the plug can be designed to last from hours to months. For example, a plug made from a hydrophilic polymer such as a lightly cross-linked PEG can last a few days, while a plug made of poly(L-lactic acid) can last many months.

Further, reverse thermosensitive bioabsorbable polymers or gels described herein can be formulated to have a very short lifetime, from minutes to hours. It is within the scope of the present description that the polymer last less than an hour. For example, a reverse thermosensitive polymer gel such as LEGOO™ (Pluromed, Inc., Woburn, Mass.) forms a plug at physiological temperature lasting less than an hour. The plug can further be removed at any time with a cold saline flush, which reverts the gel to the liquid state and the liquid gel can be expelled from the body through normal means.

Plugs and/or encasements described herein that partially impede blood flow, generally allow ample blood flow through the treated area to allow normal functioning of the vascular network in the area. For example, the partial impedance can allow 50%, 60%, 70%, 80% or 90% or more of normal blood flow through the vessel. Normal blood flow or normal functioning as used herein are defined as normal to the condition of the vessel prior to treatment. So allowing 50% of blood flow is based on a potentially limited blood flow before the procedure starts.

The present embodiments described herein relate to a catheter having multiple lumens that can deliver at least one bioactive material and at least one polymer to a target site in the vasculature of a patient in need thereof.

The dimensions, materials, and construction of the catheter body generally may vary widely and will depend on the target site itself, and the particular treatment and polymers utilized. In some instances, the average outside diameter of the catheter tubular member may range from about 1 Fr to about 15 Fr. The unit of measure "Fr" is a commonly used measure of the diameter of a catheter with a conversion of about 1 Fr≈0.33 mm. The outside diameter may stay uniform from the proximal end to the distal end or may taper so that the outside diameter of the distal end is significantly smaller than that of the proximal end. For example, the outside diameter of the proximal end may range from about 1.5 Fr to about 25 Fr, while the outside diameter of the distal end may range from about 1 Fr to about 6 Fr. The described tapering may occur gradually or at one or more distinct points along the tubular member.

The diameter of each lumen may also vary depending on the bioactive materials and polymers used and similar to the outside diameter, may taper gradually or at distinct points longitudinally along the tubular member. In some uses, the average diameter of the first lumen may range from about 0.2 Fr to about 10 Fr and may stay uniform from the proximal to the distal end. More specifically, the first lumen average diameter may range from about 1 Fr to about 6 Fr. In other uses, the average diameter of the first lumen may taper and range from about 0.5 Fr to about 15 Fr at the proximal end, and from about 0.2 Fr to about 4 Fr at the distal end. More specifically, the first lumen average diameter may range from about 2 Fr to about 12 Fr at the proximal end, and from about 0.5 Fr to about 3 Fr at the distal end.

The catheter shaft is generally constructed of materials that are highly flexible yet stiff enough to progress the catheter through a blood vessel in a controlled manner from a position far from the distal end. The shaft, for example, may comprise polymeric or silicone materials. The shaft typically is more rigid proximally so it can endure the stress exerted on it when the catheter is inserted and advanced into the vasculature yet with a low enough viscosity to advance through the vasculature. Thus, the proximal shaft may be formed from polymeric materials with low friction characteristics such as, for example, high density polyethylene, polyimide, polyamides, polyolefins, polyethylene block amide (PEBAX®) copolymer and various other polymeric materials suitable for use in medical devices.

The catheters described herein can have multiple lumens each with one or more exit ports. The exit ports can be arranged based on a particular procedure. In one embodiment, a lumen can include at least one exit port about 2 mm to about 20 mm proximal to the distal end of the catheter. In another embodiment, the lumen can include at least one exit port about 5 mm to about 10 mm proximal to the distal end of the catheter.

The catheter shaft or the tubing of the catheter system may be insulated or comprise one or more electrodes useful for delivering energy in a particular form. Electrode(s) on the distal end of the catheter for example, can be used to deliver energy in the form of heat, radio waves, microwaves or light to treat the tissue to be treated by the at least one bioactive material or to aid in curing of the at least one polymer delivered to the target site. For example, the electrode(s) may deliver radio frequency (RF) electrical energy to coagulate, ablate, or otherwise treat the surrounding tissue before treatment. In another embodiment, energy may be delivered to cure or form the at least one polymeric material being delivered at the target site. For example, UV light can be used to cure photosensitive polymers. In another example embodiment, heat can be applied to thermosensitive polymers. Energy can also be applied as the catheter is removed from the treatment site. This application of energy as the catheter system is withdrawn would facilitate solidification of polymers dependent on energy for solidification if such polymers were employed before removal of the energy source from the target site.

A proximal hub may be provided at the proximal end of the elongated tubular member. The hub may serve to provide access to the multiple lumens, typically including at least one entry port for each lumen. Each entry port may comprise a luer connector to which a delivery device may attach. In one embodiment, the entry port(s) at the proximal end of each lumen comprise a female luer fitting for attachment of a male luer fitting delivery device. The mating luer fittings serve as coupling means for coupling the proximal end of each lumen with a delivery device. Caps may be used to close the openings of the luer fittings when not attached to a delivery device.

The catheter system is intended for use in combination with a separate, movable guidewire of the type commonly used in medical procedures, particularly intravascular procedures. The movable guidewire is typically introduced percutaneously or through an open surgical incision and advanced to the target location. The delivery catheter is then introduced over the guidewire and is positioned at the target location.

If a clinician is practicing methods described herein using a minimally invasive or percutaneous technique, he/she may need some sort of real-time visualization or navigation to ensure site-specific injections. Thus, at least one embodiment uses common navigational technologies to superimpose preoperative magnetic resonance imaging (MRI) or computed tomography (CT) images onto fluoroscopic images of a delivery catheter to track it in real-time to target sites.

In one embodiment, the clinician uses a contrast agent and/or navigation technologies to track the needle-tip during injection in a virtual three-dimensional environment. This technique marks previous injections to ensure proper spacing of future injections. This is particularly important as injection of polymer or bioactive material as described herein needs to be at the target site in order for the therapy to be useful. In another embodiment, the catheters as contemplated by the present disclosure include mapping catheters such as those that can be used in conjunction with the NOGA® XP (Cordis Inc., Johnson & Johnson Company) system. One of ordinary skill in the art is generally familiar with obtaining information via mapping catheters.

Some example embodiments can include sensors and other means to assist in directing the delivery device to a desired location and ensuring that the delivery device is properly situated at the treatment site. For example, real-time recording of electrical activity (e.g., EKG), pH, oxygenation, metabolites such as lactic acid, $CO_2$, or other local indicators of cardiac tissue viability or activity can be used to help guide cell delivery. In some embodiments, the delivery device may include one or more sensors. For example, the sensors may be one or more electrical sensors, fiber optic sensors, chemical sensors, imaging sensors, structural sensors and/or proximity sensors that measure various parameters during therapy or treatment as described herein.

A catheter system as described herein may be introduced endovascularly into a blood vessel until the distal portion is at, distal to or adjacent to the desired target site. Alternatively, the catheter system may be introduced into tissue and traverse endovascularly only in certain portions until its distal portion is at, distal to, or adjacent to the desired target site. The location or target site will be predetermined and can vary for each treatment, depending on the target site and the desired effect. One skilled in the art will understand how to plan such a procedure depending on the parameters.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Accordingly, the present invention is not limited to that precisely as shown and described.

We claim:

1. A method of delivering at least one bioactive material to a vessel having a vessel wall and a vessel lumen, the method comprising the steps of:
   (a) selecting a target site within the vessel at the vessel wall in need of the at least one bioactive material;
   (b) providing a catheter comprising:
   an elongated tubular member having a distal end and a proximal end, wherein the proximal end is attached to at least one delivery means;
   a first lumen longitudinally traversing through the elongated tubular member having the ability to receive at least one bioactive material, wherein the first lumen includes an exit port at the distal end; and
   a second lumen longitudinally traversing through the elongated tubular member having the ability to receive at least one polymer, wherein the second lumen includes at least one exit port proximal to the distal end;
   (c) positioning the distal end of the catheter within the vessel lumen so that the distal end of the catheter is distal to the target site;
   (d) delivering the at least one polymer through the at least one exit port in the second lumen creating a first plug member within the vessel lumen;
   (e) repositioning the catheter so that the distal end is proximal to the first plug member;
   (f) delivering the at least one bioactive material through the exit port in the first lumen proximal the first plug member; and
   (g) removing the catheter from the vessel thereby delivering the at least one bioactive material;
   wherein the steps (e) and (f) are performed concurrently, the method further comprising delivering the at least one polymer through the at least one exit port in the second lumen concurrently with the steps (e) and (f).

2. The method of claim 1 further including a step following step (f) of delivering the at least one polymer through the at least one exit port creating a second plug member.

3. The method of claim 1, further comprising:
(h) repositioning the catheter so that the distal end is proximal to the delivered at least one bioactive material;
(i) delivering the at least one polymer through the at least one exit port and the second lumen to create an additional plug member; and
repeating the steps (e), (f), (h), and (i) to create additional plug members proximal to the first plug member and wherein the one or more bioactive materials are delivered between the additional plug members.

4. The method of claim 1, wherein the at least one polymer is selected from the group consisting of a cellulose polymer, poly(N,N-diethylacrylamide) (PDEAAm), poly (N-iso-propylacrylamide) (PNIPAM) co-polymers, poloxamer systems, PEO/D,L-lactic acid-co-glycolic acid (PLGA) hydrogels, calcium loaded liposomes (CLL) which form gels when combined, CLL with FEK16, poly (organophosphazene) derivatives, poly(1,2-propylene) phosphate and combinations thereof.

5. The method of claim 1 or 2, wherein said catheter further comprises at least one electrode to provide energy to the target site or the at least one polymer adjacent to the catheter.

6. The method of claim 5 further including a step following the delivery of the at least one polymer wherein energy is provided to the at least one polymer to gel or solidify the at least one polymer.

7. The method of claim 1, wherein the at least one polymer is fluent in the second lumen and becomes less-fluent when delivered to the target site.

8. The method of claim 1, wherein the at least one polymer solidifies after delivery to the target site.

9. The method of claim 1, wherein the delivery means includes at least two entry ports.

10. The method of claim 1, wherein the at least one bioactive material is selected from the group consisting of embryonic cells, fetal cells, post-natal cells, adult stem cells, progenitor cells and combinations thereof.

11. The method of claim 1 further comprising delivering the at least one polymer through the at least one exit port creating a second plug member proximal the target site, the first plug member and the second plug member defining a passage to allow continued blood flow through the vessel lumen.

12. A method of delivering at least one bioactive material to a vessel having a vessel wall and a vessel lumen, the method comprising the steps of:
(a) selecting a target site within the vessel at the vessel wall in need of the at least one bioactive material;
(b) providing a catheter comprising:
an elongated tubular member having a distal end and a proximal end, wherein the proximal end is attached to at least one delivery means;
a first lumen longitudinally traversing through the elongated tubular member having the ability to receive at least one bioactive material, wherein the first lumen includes an exit port at the distal end; and
a second lumen longitudinally traversing through the elongated tubular member having the ability to receive at least one polymer, wherein the second lumen includes at least one exit port proximal to the distal end;
(c) positioning the distal end of the catheter within the vessel lumen so that the distal end of the catheter is distal to the target site;
(d) delivering the at least one polymer through the at least one exit port in the second lumen creating a first plug member within the vessel lumen;
(e) repositioning the catheter so that the distal end is proximal to the first plug member;
(f) delivering the at least one polymer through the at least one exit port to create a second plug member;
(g) delivering the at least one bioactive material through the exit port in the first lumen proximal the first plug member between the first plug member and the second plug member; and
(h) removing the catheter from the vessel thereby delivering the at least one bioactive material.

13. The method of claim 12, wherein the at least one polymer is selected from the group consisting of a cellulose polymer, poly(N,N-diethylacrylamide) (PDEAAm), poly (N-iso-propylacrylamide) (PNIPAM) co-polymers, poloxamer systems, PEO/D,L-lactic acid-co-glycolic acid (PLGA) hydrogels, calcium loaded liposomes (CLL) which form gels when combined, CLL with FEK16, poly (organophosphazene) derivatives, poly(1,2-propylene) phosphate and combinations thereof.

14. The method of claim 12, wherein said catheter further comprises at least one electrode to provide energy to the target site or the at least one polymer adjacent to the catheter.

15. The method of claim 14 further including a step following the delivery of the at least one polymer wherein energy is provided to the at least one polymer to gel or solidify the at least one polymer.

16. The method of claim 12, wherein the at least one polymer is fluent in the second lumen and becomes less-fluent when delivered to the target site.

17. The method of claim 12, wherein the at least one polymer solidifies after delivery to the target site.

18. The method of claim 12, wherein the delivery means includes at least two entry ports.

19. The method of claim 12, wherein the at least one bioactive material is selected from the group consisting of embryonic cells, fetal cells, post-natal cells, adult stem cells, progenitor cells and combinations thereof.

* * * * *